United States Patent
Park et al.

(10) Patent No.: US 7,225,021 B1
(45) Date of Patent: May 29, 2007

(54) DIFFERENTIATION OF CENTRAL SLEEP APNEA AND OBSTRUCTIVE SLEEP APNEA USING AN IMPLANTABLE CARDIAC DEVICE

(75) Inventors: Euljoon Park, Valencia, CA (US); Steve Koh, South Pasadena, CA (US)

(73) Assignee: Pacesetter, Inc., Sylmar, CA (US)

( * ) Notice: Subject to any disclaimer, the term of this patent is extended or adjusted under 35 U.S.C. 154(b) by 197 days.

(21) Appl. No.: 10/769,165

(22) Filed: Jan. 30, 2004

(51) Int. Cl.
 *A61N 1/05* (2006.01)

(52) U.S. Cl. .................... 607/18; 607/20; 607/42; 607/62; 600/484; 600/529; 600/538; 600/301

(58) Field of Classification Search ............... 607/18, 607/20, 42, 62; 600/301, 484, 538, 529
See application file for complete search history.

(56) References Cited

U.S. PATENT DOCUMENTS

| | | | | |
|---|---|---|---|---|
| 4,506,678 A | * | 3/1985 | Russell et al. | 600/536 |
| 4,576,183 A | * | 3/1986 | Plicchi et al. | 600/536 |
| 4,721,110 A | * | 1/1988 | Lampadius | 607/20 |
| 4,830,008 A | * | 5/1989 | Meer | 607/42 |
| 5,146,918 A | | 9/1992 | Kallok et al. | 128/419 G |
| 5,385,144 A | * | 1/1995 | Yamanishi et al. | 600/330 |
| 5,476,483 A | | 12/1995 | Bornzin et al. | 607/17 |
| 5,540,732 A | * | 7/1996 | Testerman | 607/42 |
| 5,671,733 A | * | 9/1997 | Raviv et al. | 600/301 |
| 5,704,345 A | * | 1/1998 | Berthon-Jones | 128/204.23 |
| 5,974,340 A | | 10/1999 | Kadhiresan | 607/18 |
| 6,126,611 A | * | 10/2000 | Bourgeois et al. | 600/529 |
| 6,223,064 B1 | * | 4/2001 | Lynn et al. | 600/324 |
| 6,345,202 B2 | * | 2/2002 | Richmond et al. | 607/42 |
| 6,375,623 B1 | * | 4/2002 | Gavriely | 600/534 |
| 6,580,944 B1 | * | 6/2003 | Katz et al. | 600/513 |
| 6,731,984 B2 | * | 5/2004 | Cho et al. | 607/17 |
| 6,881,192 B1 | * | 4/2005 | Park | 600/529 |

FOREIGN PATENT DOCUMENTS

EP  0505195 B1  11/1997

\* cited by examiner

*Primary Examiner*—Robert E. Pezzuto
*Assistant Examiner*—Deborah Malamud (57) ABSTRACT

An implantable cardiac device is programmed to differentiate between central sleep apnea and obstructive sleep apnea. The implantable cardiac device utilizes a respiration-related parameter (e.g., respiration rate, tidal volume, and minute ventilation) to determine whether the patient is experiencing an episode of sleep apnea. When sleep apnea is detected, the implantable cardiac device examines the intracardiac electrogram (IEGM) to classify the apnea as either central sleep apnea or obstructive sleep apnea. The cardiac device may be further configured to administer different therapies depending upon the classification of sleep apnea.

21 Claims, 4 Drawing Sheets

DIFFERENTIATION OF CENTRAL SLEEP APNEA AND OBSTRUCTIVE SLEEP APNEA USING AN IMPLANTABLE CARDIAC DEVICE

TECHNICAL FIELD

The present invention generally relates to implantable cardiac devices, and particularly, to techniques for differentiating between central sleep apnea and obstructive sleep apnea.

BACKGROUND

Sleep apnea is a condition in which a person stops breathing for a short time while sleeping. Symptoms of sleep apnea include snoring, breath holding during sleep, rapid awakening with gasping for air, morning headaches, depression, irritability, loss of memory, lack of energy, high risk of automobile and workplace accidents, and lack of high quality sleep and resulting daytime grogginess and sleepiness. Sleep apnea is rarely fatal but is linked to high blood pressure and increased probability of heart disease, stroke, and arrhythmias. Patients with coronary artery disease who have a blood oxygen level lowered by sleep-disordered breathing may be at risk of ventricular arrhythmia and nocturnal sudden death. Furthermore, sleep-disordered breathing may cause coronary artery disease and hypertension.

There are different classifications of sleep apnea depending upon the source of dysfunction. Obstructive sleep apnea results from mechanical blockage of the airway, for example, due to weight of fatty neck tissue compressing the trachea or decrease of muscle tone during sleep. Central sleep apnea results from neurological dysfunction. Another reason for central sleep apnea is lung-to-chemoreflex $CO_2$ sensor located in carotid body. The decreased cardiac output will delay the circulatory time which affect the feedback delay time resulting oscillatory behavior in respiratory controller.

Various treatments exist for sleep apnea including medical device treatments, surgery, and drugs. The type of treatment depends on the classification of sleep apnea. For patients who also experience heart failure or other cardiac conditions, implantable cardiac devices (e.g., implantable pacemaker or defibrillator) have been proposed for treating sleep apnea through the use of high rate pacing therapy. It would be advantageous for such devices to be capable of differentiating between central sleep apnea and obstructive sleep apnea for diagnostic purposes or to administer the appropriate responsive therapies.

SUMMARY

An implantable cardiac device is programmed to differentiate between central sleep apnea and obstructive sleep apnea. In one implementation, the implantable cardiac device utilizes a respiration-related parameter (e.g., respiration rate, tidal volume, minute ventilation, and the like) to determine whether the patient is experiencing an episode of sleep apnea. When sleep apnea is detected, the implantable cardiac device examines the intracardiac electrogram to classify the apnea as either central sleep apnea or obstructive sleep apnea. Under the control of a physician, the cardiac device may be further configured to administer different therapies depending upon the classification of sleep apnea.

DETAILED DESCRIPTION

Overview

The following discussion describes an implantable cardiac device that differentiates between central sleep apnea and obstructive sleep apnea. The device is programmed to detect when a patient experiences an episode of sleep apnea based on changes in respiration (e.g., respiration rate, tidal volume, and minute ventilation). Once sleep apnea is detected, the device examines the patient's intracardiac electrogram (IEGM) to distinguish between central and obstructive sleep apnea. The IEGM waveform exhibits different amplitude modulation patterns over the respiratory cycle depending upon whether the apnea is central-based or obstructive-based. The device can be optionally programmed to administer various pacing therapies depending upon the classification of sleep apnea.

Implantable cardiac devices are commonly characterized as a miniature computing device that is implanted into the body of a patient to monitor, regulate, and/or correct heart activity. Such devices include implantable cardiac stimulation devices (e.g., implantable cardiac pacemakers, implantable defibrillators, cardiac rhythm management devices) that apply stimulation therapy to the heart and implantable cardiac monitors that monitor and record heart activity for diagnostic purposes. The following discussion describes first an exemplary cardiac device and then a mode of operation in which sleep apnea episodes are detected and classified as either obstructive sleep apnea or central sleep apnea.

Implantable Cardiac System

Figure 1:
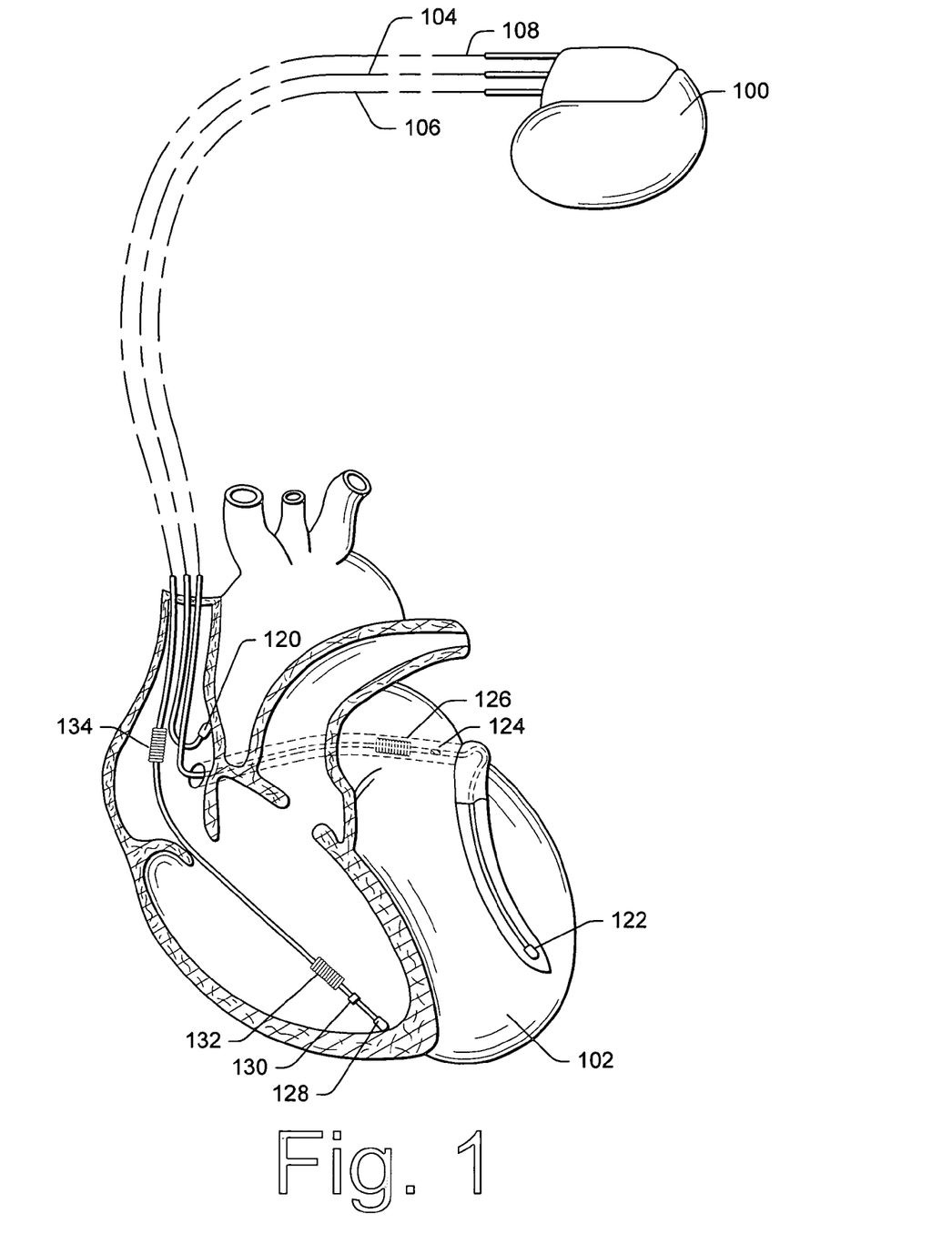
FIG. 1 is a diagrammatic illustration of an implantable cardiac device in electrical communication with a patient's heart for multi-chamber sensing and delivery of multi-chamber stimulation and shock therapy.

FIG. 1 shows an exemplary implantable cardiac device 100 in electrical communication with a patient's heart 102 for monitoring heart activity and/or delivering stimulation therapy, such as pacing therapies. Three leads—a right atrial lead 104, a coronary sinus lead 106, and a right ventricular lead 108—interconnect the device 100 with the patient's heart 102 to support multi-chamber detection and stimulation therapy.

The right atrial lead 104 supports an atrial tip electrode 120, which typically is implanted in the patient's right atrial appendage. The right atrial lead 104 enables the device to sense atrial cardiac signals and apply pacing therapy to the right atrial chamber.

The coronary sinus lead 106 positions a left ventricular tip electrode 122 adjacent to the left ventricle and/or additional electrode(s) adjacent to the left atrium, such as a left atrial ring electrode 124 and a left atrial coil electrode 126. The coronary sinus lead 106 enables the device 100 to sense left atrial and ventricular cardiac signals and administer left chamber pacing therapy. In the illustrated arrangement, the left ventricular tip electrode 122 is used to sense atrial and ventricular cardiac signals and deliver left ventricular pacing therapy. The left atrial ring electrode 124 is employed for applying left atrial pacing therapy, and the left atrial coil electrode 126 is used for shocking therapy.

The right ventricular lead 108 is electrically coupled to a right ventricular tip electrode 128, a right ventricular ring electrode 130, a right ventricular (RV) coil electrode 132, and an SVC coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of receiving cardiac signals, and delivering stimulation in the form of pacing and shock therapy to the right ventricle.

Figure 2:
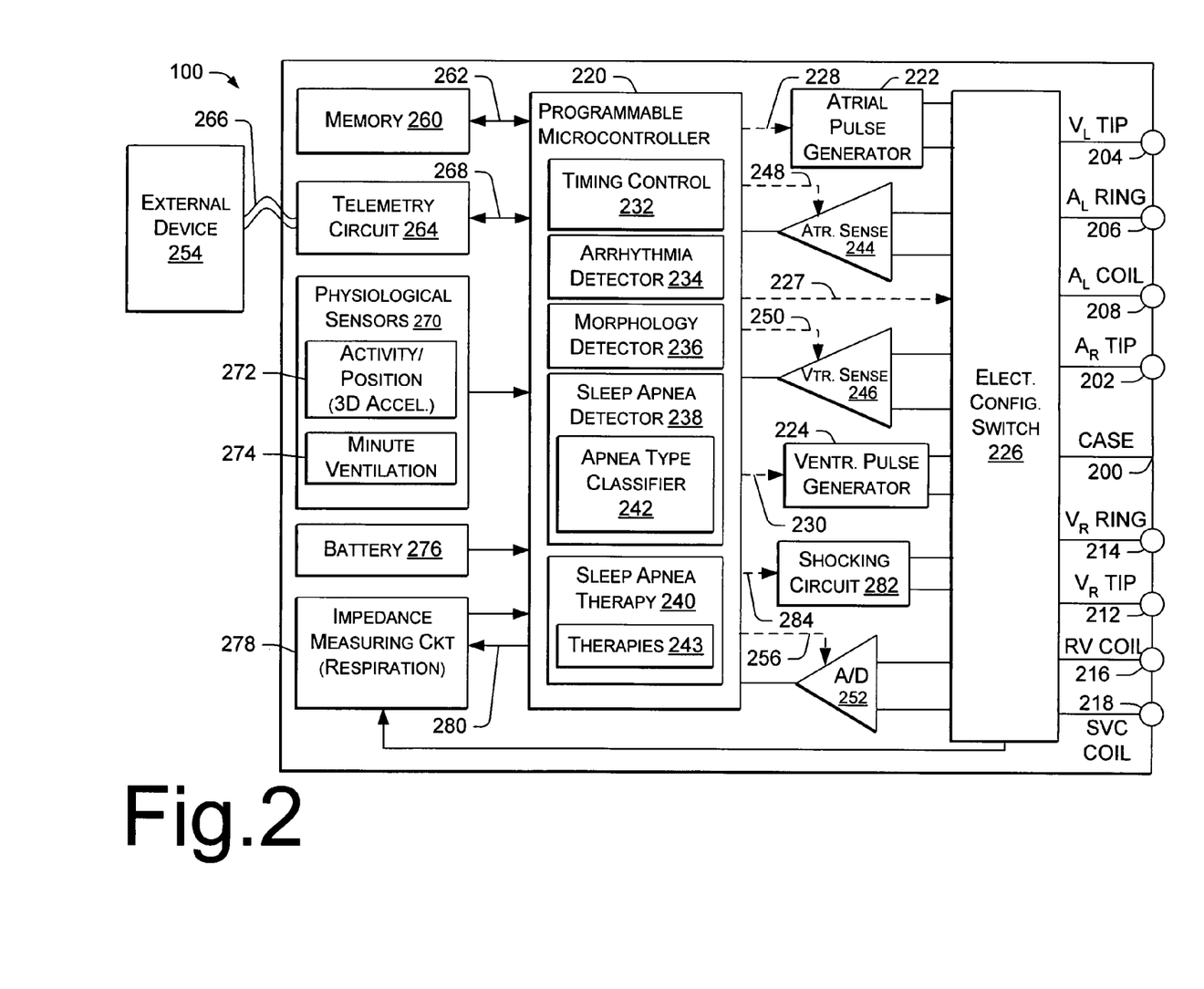
FIG. 2 is a functional block diagram of the multi-chamber implantable cardiac device.

FIG. 2 shows an exemplary, simplified block diagram depicting various components of the implantable cardiac device 100. The components are housed in housing 200, which is often referred to as the "can", "case", "encasing", or "case electrode". Housing 200 may be programmably selected as a return electrode for unipolar modes or in combination with one or more of the coil electrodes 126, 132 and 134 for shocking purposes. Housing 200 further includes a connector (not shown) having a plurality of terminals 202, 204, 206, 208, 212, 214, 216, and 218 (shown schematically and, for convenience, the names of the electrodes to which they are connected are shown next to the terminals), including:

a right atrial tip terminal (AR TIP) 202 for atrial tip electrode 120;

a left ventricular tip terminal (VL TIP) 204 for left ventricular tip electrode 122;

a left atrial ring terminal (AL RING) 206 for left atrial ring electrode 124;

a left atrial shocking terminal (AL COIL) 208 for left atrial coil electrode 126;

a right ventricular tip terminal (VR TIP) 212 for right ventricular tip electrode 128;

a right ventricular ring terminal (VR RING) 214 for right ventricular ring electrode 130;

a right ventricular shocking terminal (RV COIL) 216 for RV coil electrode 132; and an SVC shocking terminal (SVC COIL) 218 for SVC coil electrode 134.

The implantable cardiac device 100 includes a programmable microcontroller 220 that controls various operations, including cardiac monitoring and stimulation therapy. Microcontroller 220 includes a microprocessor (or equivalent control circuitry), RAM and/or ROM memory, logic and timing circuitry, state machine circuitry, and I/O circuitry.

Device 100 further includes an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. The switch 226 includes multiple switches for connecting the desired electrodes to the appropriate I/O circuits, thereby providing complete electrode programmability. Accordingly, switch 226, in response to a control signal 227 from the microcontroller 220, determines the polarity of the stimulation pulses (e.g., unipolar, bipolar, combipolar, etc.) by selectively closing the appropriate combination of switches. To provide stimulation therapy in each of the four chambers of the heart, the atrial and ventricular pulse generators 222 and 224 may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 is illustrated as including timing control circuitry 232 to control the timing of the stimulation pulses (e.g., pacing rate, atrio-ventricular (AV) delay, atrial interconduction (A—A) delay, or ventricular interconduction (V—V) delay, etc.). The timing control circuitry may also be used for the timing of refractory periods, blanking intervals, noise detection windows, evoked response windows, alert intervals, marker channel timing, and so on.

Microcontroller 220 is equipped with an arrhythmia detector 234 and a morphology detector 236 to evaluate various data collected by the cardiac device in an effort to detect arrhythmia and morphological events. A sleep apnea detector 238 and a sleep apnea therapy module 240 are also implemented by the microcontroller 220. The sleep apnea detector 238 is configured to detect episodes of sleep apnea that occur while the patient is at rest. In one implementation, the sleep apnea detector 238 uses changes in respiration-related data to detect episodes of sleep apnea. Such respiration-related data might include, for example, respiration rate, tidal volume, minute ventilation, respiration signal amplitude, and the like.

The sleep apnea detector 238 implements an apnea type classifier module 242 to differentiate between obstructive sleep apnea and central sleep apnea. In one implementation, the apnea type classifier module 242 examines intracardiac electrogram (IEGM) data to distinguish between the two types of apnea. The IEGM data exhibits different patterns depending upon the type of apnea. For obstructive sleep apnea, the patient's breathing is occluded by physical blockage, but the patient still makes an effort to breath. During obstructive sleep apnea, the patient's diaphragm attempts respiratory effort, causing the evoked response waveform of the IEGM to exhibit observable amplitude modulation over several beats of the respiratory cycle. In contrast, for central sleep apnea, the patient does not attempt respiratory effort. This causes the IEGM pattern to exhibit no significant modulation. The apnea type classifier module 242 is calibrated to distinguish between the presence and absence of amplitude modulation in the IEGM signal.

The sleep apnea therapy module 240 prescribes one or more pacing therapies 243 that can be administered in response to detection and/or classification of sleep apnea. For example, for central sleep apnea, the therapies might include overdrive pacing in which the pacing rate is increased by some fixed or adjustable amount. The responsive pacing may be applied for a period of time, or a predetermined number of beats, or until the sleep apnea episode has concluded. The therapies might call for different degrees of gradually decreasing the pacing rate to the intrinsic rate of the resting patient. For obstructive sleep apnea, the therapies might include overdrive pacing, stimulation of the phrenic nerve, and diaphragm stimulation. Another possible therapy is to apply upper airway nervous or muscular stimulation, such as stimulating a region under the tongue to maintain muscle tone in upper airway. One technique for stimulating the diaphragm or musculature of the upper airway is described in U.S. Pat. No. 5,146,918.

The components 234–243 may be implemented in hardware as part of the microcontroller 220, or as software/firmware instructions programmed into the device and executed on the microcontroller 220 during certain modes of operation. These components 234–243 may further be implemented independent from the microcontroller 220. Although not shown, the microcontroller 220 may further include other dedicated circuitry and/or firmware/software components that assist in monitoring various conditions of the patient's heart and managing pacing therapies.

Atrial sensing circuits 244 and ventricular sensing circuits 246 may also be selectively coupled to the right atrial lead 104, coronary sinus lead 106, and the right ventricular lead 108, through the switch 226 to detect the presence of cardiac activity in each of the four chambers of the heart. The sensing circuits 244 and 246 may include dedicated sense amplifiers, multiplexed amplifiers, or shared amplifiers. Switch 226 determines the "sensing polarity" of the cardiac signal by selectively closing the appropriate switches. In this way, the clinician may program the sensing polarity independent of the stimulation polarity. Each sensing circuit 244 and 246 may employ one or more low power, precision amplifiers with programmable gain and/or automatic gain control, band pass filtering, and threshold detection circuitry to selectively sense the cardiac signal of interest. The automatic gain control enables the device 100 to sense low amplitude signal characteristics of atrial or ventricular fibrillation.

The outputs of the atrial and ventricular sensing circuits 244 and 246 are connected to the microcontroller 220 which, in turn, is able to trigger or inhibit the atrial and ventricular pulse generators 222 and 224 in response to the absence or presence of cardiac activity in the appropriate chambers of the heart. The sensing circuits 244 and 246 receive control signals from the microcontroller 220 over signal lines 248 and 250 for purposes of controlling the gain, threshold, polarization charge removal circuitry (not shown), and the timing of any blocking circuitry (not shown) coupled to the inputs of the sensing circuits.

Cardiac signals are supplied to an analog-to-digital (A/D) data acquisition system 252, which is configured to acquire intracardiac electrogram (IEGM) signals, convert the raw analog data into a digital signal, and store the digital signals for pattern analysis by the apnea type classifier 242, for other types of processing and/or for telemetric transmission to an external device 254. The data acquisition system 252 is coupled to the right atrial lead 104, the coronary sinus lead 106, and the right ventricular lead 108 through the switch 226 to sample cardiac signals across any pair of desired electrodes.

The data acquisition system 252 is coupled to the microcontroller 220, or other detection circuitry, to assist in detecting an evoked response from the heart 102 in response to an applied stimulus, which is otherwise known as detecting "capture". Capture occurs when an electrical stimulus applied to the heart is of sufficient energy to depolarize the cardiac tissue, thereby causing the heart muscle to contract. The microcontroller 220 detects a depolarization signal during a window following a stimulation pulse, the presence of which indicates that capture has occurred. The microcontroller 220 enables capture detection by triggering the ventricular pulse generator 224 to generate a stimulation pulse, starting a capture detection window using the timing control circuitry 232 within the microcontroller 220, and enabling the data acquisition system 252 via control signal 256 to sample the cardiac signal that falls in the capture detection window and, based on the amplitude, determines if capture has occurred.

Capture detection may occur on a beat-by-beat basis or on a sampled basis. A capture threshold search can desirably be performed once a day during at least the acute phase (e.g., the first 30 days) and less frequently thereafter. A capture threshold search would begin at a desired starting point (either a high energy level or the level at which capture is currently occurring) and decrease the energy level until capture is lost. The value at which capture is lost is known as the capture threshold. Thereafter, a safety margin is added to the capture threshold.

The microcontroller 220 is further coupled to a memory 260 by a suitable data/address bus 262. The programmable operating parameters used by the microcontroller 220 are stored in memory 260 and used to customize the operation of the device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 102 within each respective tier of therapy.

The operating parameters of the implantable device 100 may be non-invasively programmed into the memory 260 through a telemetry circuit 264 in telemetric communication via communication link 266 with the external device 254. The external device 254 may be implemented in many ways, including as a programmer, a transtelephonic transceiver, or a diagnostic system analyzer. The microcontroller 220 activates the telemetry circuit 264 with a control signal 268. The telemetry circuit 264 allows intracardiac electrograms and status information relating to the operation of the device 100 (as contained in the microcontroller 220 or memory 260) to be sent to the external device 254 through an established communication link 266.

The implantable cardiac device 100 can further include one or more physiologic sensors 270. Such sensors are commonly referred to as "rate-responsive" sensors because they are typically used to adjust pacing stimulation rates according to the exercise state of the patient. However, the physiological sensor(s) 270 may further be used to detect changes in cardiac output, changes in the physiological condition of the heart, diurnal changes in activity (e.g., detecting sleep and wake states), or respiration activity (e.g., minute ventilation). The microcontroller 220 responds to changes sensed by the sensor(s) 270 by adjusting various pacing parameters (such as rate, AV Delay, V—V Delay, etc.) at which the atrial and ventricular pulse generators 222 and 224 generate stimulation pulses. While shown as being included within the device 100, the physiologic sensor(s) 270 may also be external to the device 100, yet still be implanted within or carried by the patient. Examples of physiologic sensors that may be implemented in device 100 include sensors that, for example, sense respiration activities, O2 saturation, evoked response, pH of blood, and so forth.

In the illustrated implementation, the physiological sensors 270 include sensors for detecting patient activity and respiration. Any sensor capable of sensing such conditions, either directly or indirectly, may be used. In particular, the physiological sensors 270 include an activity sensor 272 to detect patient movement. The activity sensor 272 may be implemented in many ways, including as a three-dimensional (3D) DC accelerometer. In one configuration, the accelerometer output signal is bandpass-filtered, rectified, and integrated at regular timed intervals. The processed accelerometer signal is used as a raw activity signal. The device derives an activity measurement based on the raw activity signal at intervals timed according to the cardiac cycle. The activity signal alone can be used to indicate whether a patient is active or resting. The activity measurement can further be used to determine an activity variance parameter. A large activity variance signal is indicative of a prolonged exercise state. Low activity and activity variance signals are indicative of a prolonged resting state. The activity variance can be monitored diurnally to detect the low variance in the measurement corresponding to the sleep state. For a complete description of the activity variance sensor, the reader is directed to U.S. Pat. No. 5,476,483 (Bornzin et al.), issued Dec. 19, 1995, which is hereby incorporated by reference.

An exemplary physiological sensor used to detect respiratory conditions is a minute ventilation (MV) sensor 274. The MV sensor 274 senses minute ventilation, which is the total volume of air that moves into and out of a patient's lungs in a minute. The MV sensor 274 uses transthoracic impedance, which is a measure of impedance across the chest cavity, to sense air movement. Lungs filled with air have higher impedance than empty lungs. Thus, upon inhalation, impedance increases and upon exhalation, impedance decreases. Other respiration sensors that may be used in addition to, or instead of, the MV sensor 274 include an O2 sensor that measures oxygen-related parameters, a sensor to measure respiration rate, and a sensor to measure tidal volume.

The activity and respiratory signals generated by the sensors 270 are passed to the microcontroller 220 for analysis by the sleep apnea detector 238. Such signals can be used to determine whether the patient is at rest and whether the patient is experiencing an episode of sleep apnea. Once rest and apnea are confirmed, the sleep apnea classifier 242 observes the IEGM signal to identify which type of sleep apnea is being experienced. Based on this classification, the sleep apnea therapy module 240 decides whether to invoke any responsive therapy.

The implantable cardiac device 100 additionally includes a battery 276 to supply operating power to various components shown in FIG. 2. The battery 276 is capable of operating at low current drains for long periods of time (e.g., less than 10 μA), and is capable of providing high-current pulses (for capacitor charging) when the patient requires a shock pulse (e.g., in excess of 2 A, at voltages above 2 V, for periods of 10 seconds or more). The battery 276 also desirably has a predictable discharge characteristic so that elective replacement time can be detected. As one example, the device 100 employs lithium/silver vanadium oxide batteries.

The device 100 can further include magnet detection circuitry (not shown), coupled to the microcontroller 220, to detect when a magnet is placed over the stimulation device 100. A magnet may be used by a clinician to perform various test functions of the stimulation device 100 and/or to signal the microcontroller 220 that the external programmer 254 is in place to receive or transmit data to the microcontroller 220 through the telemetry circuits 264.

The device 100 further includes an impedance measuring circuit 278 that is enabled by the microcontroller 220 via a control signal 280. The impedance measuring circuit 278 is used for many things, including: lead impedance surveillance during the acute and chronic phases for proper lead positioning or dislodgement; detecting operable electrodes and automatically switching to an operable pair if dislodgement occurs; measuring thoracic impedance for determining shock thresholds; detecting when the device has been implanted; measuring stroke volume; and detecting the opening of heart valves; and so forth. In particular relevance to our ongoing discussion, the impedance measuring circuit 278 can be used to measure respiration-related parameters, such as respiration rate, minute ventilation, respiration signal amplitude, and tidal volume. The impedance measuring circuit 278 is coupled to the switch 226 so that any desired electrode may be used.

The device 100 can be operated as an implantable cardioverter/defibrillator (ICD) device, which detects the occurrence of an arrhythmia and automatically applies an appropriate electrical shock therapy to the heart aimed at terminating the detected arrhythmia. To this end, the microcontroller 220 further controls a shocking circuit 282 by way of a control signal 284. The shocking circuit 282 generates shocking pulses of low (e.g., up to 0.5 Joules), moderate (e.g., 0.5–10 Joules), or high energy (e.g., 11 to 40 Joules), as controlled by the microcontroller 220. Such shocking pulses are applied to the patient's heart 102 through at least two shocking electrodes selected, for example, from the left atrial coil electrode 126, the RV coil electrode 132, and/or the SVC coil electrode 134. As noted above, the housing 200 may act as an active electrode in combination with the RV electrode 132, or as part of a split electrical vector using the SVC coil electrode 134 or the left atrial coil electrode 126 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 Joules), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

Sleep Apnea Differentiation

Figure 3:
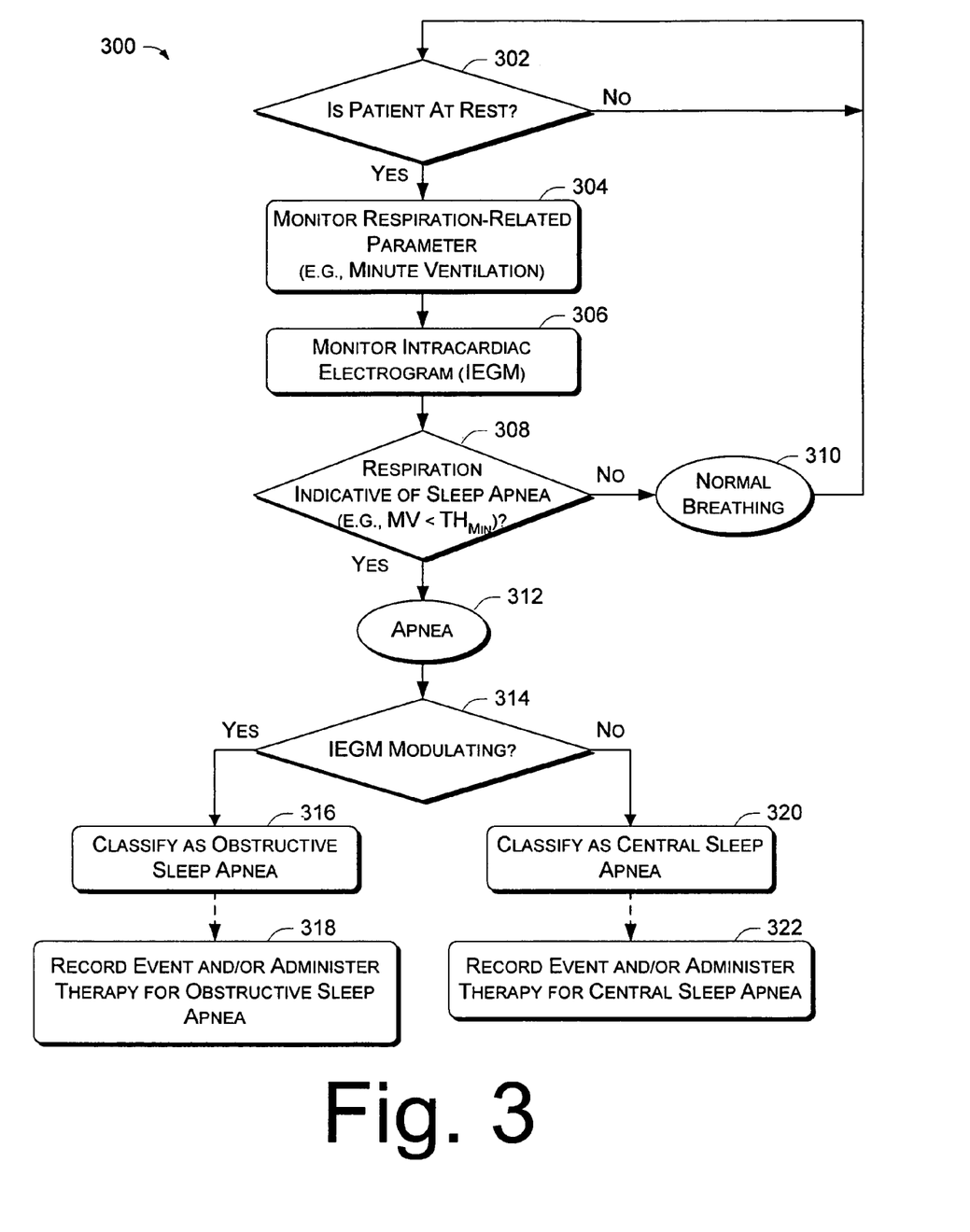
FIG. 3 is a flow diagram of a process for differentiating between central sleep apnea and obstructive sleep apnea.

FIG. 3 shows a process 300 for detecting sleep apnea episodes and differentiating whether the sleep apnea is obstructive sleep apnea or central sleep apnea. This process 300 may be implemented in connection with any suitably configured device, although it will be described as being executed by the implantable cardiac device 100 of FIGS. 1 and 2. In the flow diagram, the operations are summarized in individual blocks. The operations may be performed in hardware and/or as machine-readable instructions (software or firmware) that can be executed by a processor.

At block 302, the implantable cardiac device 100 determines whether a patient is at rest. There are many ways to implement this function. One approach is to monitor patient activity via the activity sensor 272 and confirm that a patient is at rest when the patient has been inactive for a predetermined amount of time. Another approach is to monitor respiration changes. Another technique is to detect patient position, and whether the patient is in a supine position, rather than upright. Other indicia of rest may also be utilized.

Once the patient is determined to be at rest (i.e., the "Yes" branch from block 302), the device monitors one or more respiration-related parameters associated with or indicative of the patient's respiration (block 304). In one implementation, the device monitors minute ventilation (MV) based on output from MV sensor 272. The MV signal fluctuates strongly when air is moving into and out of the pulmonary system. Alternatively, this may be accomplished in other ways, including measuring respiration rate, tidal volume, O2 saturation and so on. The device monitors such respiration-related parameters using, for example, one or more physiological sensors 270 or the impedance sensor and measuring circuit 278.

At block 306, the cardiac device 100 monitors IEGM data collected by the data acquisition system 252. The data is collected over several cycles, stored, and analyzed to identify the presence or absence of amplitude modulation as an indication of respiratory effort.

At block 308, the device determines whether the patient is experiencing an episode of sleep apnea. The device utilizes the respiration-related parameter to differentiate between normal breathing patterns and apnea patterns. In a typical sleep apnea pattern, a patient exhibits normal breathing, followed by hyperventilation and then a period of apnea. The device compares the respiration-related parameter to one or more preset thresholds to determine whether the patient is breathing normally, hyperventilating, and/or experiencing apnea. If the respiration-related parameter suggests normal breathing (i.e., the "No" branch from block 308), the patient is deemed to be breathing normally (block 310). Conversely, if the respiration-related parameter suggests little breathing (i.e., the "Yes" branch from block 308), the patient is deemed to be experiencing an episode of sleep apnea (block 312).

In one implementation, the device compares minute ventilation (MV) to a minimum threshold (THMIN). If MV does not drop below the minimum threshold (i.e., MV≧THMIN), the device decides that the patient is breathing normally (block 310). However, as air volume change lessens in the case of sleep apnea, the MV trend will eventually measure less than the preset threshold. When MV drops below the minimum threshold (i.e., MV<THMIN), the device recognizes the condition as sleep apnea (block 312).

When the patient is deemed to be at rest and experiencing an episode of sleep apnea, the device 100 examines whether the IEGM data exhibits amplitude modulations as a way of distinguishing between central and obstructive sleep apnea (block 314). The IEGM pattern analysis reveals whether any respiratory effort is being attempted by the patient's diaphragm. For obstructive sleep apnea, the patient's diaphragm attempts to breath and this respiratory effort causes the IEGM pattern to exhibit amplitude modulation over several beats. For central sleep apnea, the patient does not attempt to breath and the IEGM pattern exhibits no significant amplitude modulation.

Figure 4:
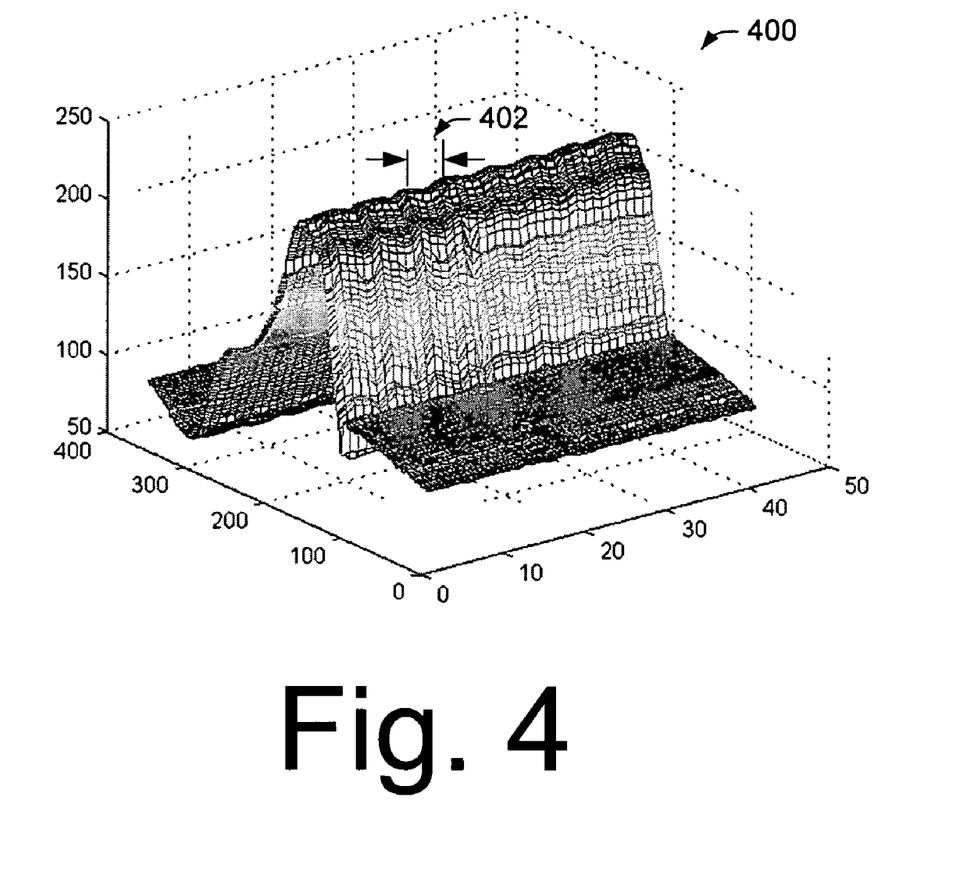
FIG. 4 shows an intracardiac electrogram pattern that is used in the differentiating process of FIG. 3.

FIG. 4 shows a three-dimensional graph 400 that plots a collection of overlapped IEGM waveforms synchronized at the V pulse for a series of consecutive heart beats. The amplitude of the evoked response varies on a beat-by-beat basis in response to respiration activity. The IEGM waveforms are plotted and rotated to provide a good viewing angle of the evoked response amplitudes and their oscillation over several respiration cycles. One respiration cycle is noted by reference 402 as including several beats end-marked by beats with peak evoked response amplitudes.

When respiration is present (as is the case for obstructive sleep apnea), there is an identifiable oscillation of the evoked response amplitudes in the IEGM pattern. This situation is represented in graph 400. Conversely, when respiration is not present (as is the case for central sleep apnea), there is no significant amplitude oscillation in the IEGM waveforms. In this case, the amplitudes of the evoked response are fairly linear.

If the IEGM exhibits a modulating pattern (i.e., the "Yes" branch from block 314), the cardiac device 100 classifies the apnea as obstructive sleep apnea (block 316). The patient is attempting respiratory effort (as represented by the IEGM modulation), but is prevented from breathing due to physical obstruction. The device 100 can optionally record the apnea event for later reporting to a physician and/or administer therapy for obstructive sleep apnea (block 318). Representative therapies might include overdrive pacing, phrenic nerve stimulation, diaphragm stimulation, and upper airway nervous or muscular stimulation.

If the IEGM does not show any significant modulation (i.e., the "No" branch from block 314), the cardiac device 100 classifies the apnea as central sleep apnea (block 320). The patient is not attempting respiratory effort (as represented by the lack of IEGM modulation) because the patient's brain believes that the body has sufficient oxygen, and hence the patient stops breathing. The device 100 can optionally record the apnea event for later reporting to a physician and/or administer therapy for central sleep apnea (block 322). Representative therapies might include overdrive pacing by increasing the pacing rate by some fixed or adjustable amount. The responsive pacing may be applied for a period of time, or a predetermined number of beats, or until the sleep apnea episode has concluded.

CONCLUSION

The foregoing discussion describes detection of sleep apnea and differentiation of central sleep apnea from obstructive sleep apnea. Although the invention has been described in language specific to structural features and/or methodological acts, it is to be understood that the subject matter defined in the appended claims is not necessarily limited to the specific features or acts described. Rather, the specific features and acts are disclosed as exemplary forms of implementing the claimed invention.

What is claimed is:

1. An implantable cardiac device comprising:
sensing circuitry to sense whether a patient is at rest, the sensing circuitry further being operative to sense cardiac electrical activity; and
a sleep apnea detector to detect when a patient, who is at rest, is experiencing an episode of sleep apnea and to differentiate between central sleep apnea and obstructive sleep apnea based on oscillation of a parameter of the cardiac electrical activity, the cardiac electrical activity comprising evoked responses over a plurality of respiration cycles.

2. An implantable cardiac device as recited in claim 1, wherein the sensing circuitry comprises an activity sensor to sense a patient's activity to determine whether the patient is at rest.

3. An implantable cardiac device as recited in claim 1, wherein the sensing circuitry comprises an accelerometer that is used to determine whether the patient is at rest.

4. An implantable cardiac device as recited in claim 1, wherein the sensing circuitry is configured to sense a respiration-related signal and the sleep apnea detector detects the episode of sleep apnea based upon the respiration-related signal.

5. An implantable cardiac device as recited in claim 4, wherein the respiration-related signal is selected from a group of signals comprising a signal indicative of tidal volume, a signal indicative of respiration rate, and a signal indicative of minute ventilation, and a signal indicative of O2 saturation.

6. An implantable cardiac device as recited in claim 1, wherein the parameter comprises an amplitude of an evoked response.

7. An implantable cardiac device as recited in claim 1, further comprising a sleep apnea therapy module to administer different pacing therapies depending upon whether the sleep apnea detector classified the sleep apnea as central sleep apnea or obstructive sleep apnea.

8. An implantable cardiac device comprising:
a sensor that indicates rest;
a sensor to sense a respiration-related parameter;

a data acquisition system to acquire an intracardiac electrogram (IEGM) signal; and a processor to detect an episode of sleep apnea based on changes in the respiration-related parameter and to differentiate between central sleep apnea and obstructive sleep apnea based on oscillation of a parameter of the IEGM signal over a plurality of respiration cycles.

9. An implantable cardiac device as recited in claim 8, wherein the rest-indicating sensor comprises at least one of an activity sensor, a position sensor, or an accelerometer.

10. An implantable cardiac device as recited in claim 8, wherein the respiration sensor comprises a minute ventilation sensor.

11. An implantable cardiac device as recited in claim 8, wherein the parameter comprises an amplitude of an evoked response and the processor analyzes the amplitudes of a plurality of evoked responses over consecutive respiration cycles, the processor classifying the episode as (1) obstructive sleep apnea when oscillation of the amplitudes is present and (2) as central sleep apnea when no significant oscillation of the amplitudes is present.

12. An implantable cardiac device as recited in claim 8, further comprising a pulse generator to generate pacing pulses, the processor prescribing different pacing therapies depending upon whether the episode is determined to be central sleep apnea or obstructive sleep apnea.

13. An implantable cardiac device comprising:
 sleep apnea detection means for detecting an episode of sleep apnea;
 data acquisition means for collecting an intracardiac electrogram signal; and
 classification means for classifying the episode as one of central sleep apnea and obstructive sleep apnea based on analysis of oscillation of a parameter of the IEGM signal over a plurality of respiration cycles.

14. An implantable cardiac device as recited in claim 13, further comprising:

sensing means for sensing a respiration signal; and wherein the sleep apnea detection means comprises means for utilizing the respiration signal to detect the episode of sleep apnea.

15. An implantable cardiac device as recited in claim 14, wherein the sensing means comprises one or more sensors selected from a group of sensors comprising a minute ventilation sensor, an impedance sensor, and a respiration sensor.

16. An implantable cardiac device as recited in claim 13, further comprising means for stimulating a heart in response to at least selected episodes of sleep apnea.

17. A method implemented by an implantable cardiac device, the method comprising:
 detecting an episode of sleep apnea; and
 classifying the episode of sleep apnea as either central sleep apnea or obstructive sleep apnea based upon oscillation of a parameter of an intracardiac electrogram (IEGM) signal over a plurality of respiration cycles.

18. A method as recited in claim 17, wherein the detecting comprises monitoring a respiration-related parameter.

19. A method as recited in claim 17, wherein the detecting comprises monitoring an oxygen-related parameter.

20. A method as recited in claim 17, wherein the parameter comprises an amplitude of an evoked response of the IEGM signal and the classifying comprises analyzing the amplitudes of a plurality of evoked responses and classifying the episode as (1) obstructive sleep apnea when oscillation of the amplitudes is present and (2) central sleep apnea when no significant oscillation of the amplitudes is present.

21. A method as recited in claim 17, further comprising administering different pacing therapies according to said classification of the episode.

* * * * *